(12) United States Patent
Cavuto et al.

(10) Patent No.: US 11,833,077 B2
(45) Date of Patent: Dec. 5, 2023

(54) MODULAR GLAUCOMA IMPLANT (71) Applicant: Massachusetts Institute of Technology, Cambridge, MA (US)

(72) Inventors: Matthew L. Cavuto, Skillman, NJ (US); Dalia P. Leibowitz, Cambridge, MA (US); Callum Joseph Macintosh, Walsall (GB)

(73) Assignee: Massachusetts Institute of Technology, Cambridge, MA (US)

( * ) Notice: Subject to any disclaimer, the term of this patent is extended or adjusted under 35 U.S.C. 154(b) by 545 days.

(21) Appl. No.: 16/622,610

(22) PCT Filed: Jun. 15, 2018

(86) PCT No.: PCT/US2018/037764
§ 371 (c)(1),
(2) Date: Dec. 13, 2019

(87) PCT Pub. No.: WO2018/232248
PCT Pub. Date: Dec. 20, 2018

(65) Prior Publication Data
US 2021/0137736 A1    May 13, 2021

Related U.S. Application Data

(60) Provisional application No. 62/520,647, filed on Jun. 16, 2017.

(51) Int. Cl.
*A61F 9/007*    (2006.01)

(52) U.S. Cl.
CPC .... *A61F 9/00781* (2013.01); *A61F 2250/006* (2013.01)

(58) Field of Classification Search
CPC ...................... A61F 9/00781; A61F 2250/006
See application file for complete search history.

(56) References Cited

U.S. PATENT DOCUMENTS

| 4,037,604 A | 7/1977 | Newkirk |
| 6,450,982 B1 | 9/2002 | Peterson |
| 6,464,724 B1 | 10/2002 | Lynch et al. |

(Continued)

OTHER PUBLICATIONS

[No Author Listed], Form S-1 Registration Statement. Inotek Pharmaceuticals Corporation. Nov. 4, 2014. Available at sec.gov/Archives/edgar/data/1281895/000119312514396875/d780115ds1.htm. 282 pages.

(Continued)

*Primary Examiner* — Benjamin J Klein
(74) *Attorney, Agent, or Firm* — Wolf, Greenfield & Sacks, P.C.

(57) ABSTRACT

A modular glaucoma implant for the treatment of glaucoma is described. Embodiments disclosed describe a glaucoma treatment device including an elongated fixation stent that allows aqueous humor to flow from the anterior chamber of the eye to the Schlemm's Canal when implanted. One or more drainage tubes can be inserted into the fixation stent such that the drainage tubes allow aqueous humor to flow from the anterior chamber of the eye to the suprachoroidal space. Surgeons can opt to add as many drainage tubes as desired based on the needed aqueous humor outflow rate.

17 Claims, 9 Drawing Sheets

(56) References Cited

U.S. PATENT DOCUMENTS

| | | | |
|---|---|---|---|
| 6,699,211 | B2 | 3/2004 | Savage |
| 7,740,604 | B2 | 6/2010 | Schieber et al. |
| 8,771,216 | B2* | 7/2014 | Orge .................. A61F 9/00781 604/9 |
| 2002/0198585 | A1 | 12/2002 | Wisselink |
| 2007/0293807 | A1* | 12/2007 | Lynch ................ A61F 9/00781 604/8 |
| 2013/0165840 | A1* | 6/2013 | Orge .................. A61F 9/00781 604/8 |
| 2016/0067092 | A1 | 3/2016 | Lind et al. |
| 2016/0331588 | A1 | 11/2016 | Ambati et al. |

OTHER PUBLICATIONS

[No Author Listed], The Current State of Medical Stent Manufacturing. Laserage.com. Jan. 15, 2016. Available at laserage.com/state-medical-stent-manufacturing/. 2 pages.

[No Author Listed], Trabeculectomy. International Glaucoma Association. 2019. Available at glaucoma-association.com/about-glaucoma/treatments/surgery/trabeculectomy. 13 pages.

[No Author Listed], Types of Glaucoma. Glaucoma Research Foundation. Oct. 29, 2017. Available at glaucoma.org/glaucoma/types-of-glaucoma.php. 2 pages.

Chen, Glaucoma Laser Treatment: Argon Laser Trabeculoplasty (ALT). Digital Journal of Ophthalmology. Jan. 13, 2003. 2 pages.

Chen, Glaucoma Laser Treatment: Laser Peripheral Iridotomy (LPI). Digital Journal of Ophthalmology. Jan. 13, 2003. 2 pages.

Emi et al., Hydrostatic pressure of the suprachoroidal space. Invest Ophthalmol Vis Sci. Feb. 1989;30(2):233-8.

Goel et al., Aqueous humor dynamics: a review. Open Ophthalmol J. Sep. 3, 2010;4:52-9. doi: 10.2174/1874364101004010052.

Kokkinakis, Narrow Down Your Chances of Developing Acute Narrow Angle Glaucoma. Optometrist.com. 2017. Available at optometrist.com.au/narrow-chances-developing-acute-narrow-angle-glaucoma/. 3 pages.

Maepea et al., The pressures in the episcleral veins, Schlemm's canal and the trabecular meshwork in monkeys: effects of changes in intraocular pressure. Exp Eye Res. Oct. 1989;49(4):645-63.

Martinez et al., Microfabrication and nanotechnology in stent design. Wiley Interdiscip Rev Nanomed Nanobiotechnol. May 2011-Jun.;3(3):256-68. doi: 10.1002/wnan.123. Epub Jan. 31, 2011. Author Manuscript.

Murdoch, Post-operative management of trabeculectomy in the first three months. Community Eye Health. 2012;25(79-80):73-5.

Ou, Glaucoma Surgery Series: Tube Shunt Drainage Devices for Glaucoma. BrightFocus Foundation. Mar. 24, 2017. Available at brightfocus.org/glaucoma/article/glaucoma-surgery-series-tube-shunt-drainage-devices-glaucoma. 8 pages.

Radhakrishnan et al., Glaucoma Medications and their Side Effects. Glaucoma Research Foundation. Jul. 23, 2018. Available at glaucoma.org/gleams/glaucoma-medications-and-their-side-effects.php. 3 pages.

Richardson, Types of Glaucoma Drainage Devices. New Glaucoma Treatments. Oct. 20, 2014. Available at new-glaucoma-treatments.com/types-of-glaucoma-drainage-devices/. 15 pages.

Schuster, How Glaucoma Affects the Optic Nerve. Glaucoma Research Foundation. Jul. 4, 2017. Available at glaucoma.org/glaucoma/the-optic-nerve-questions-and-answers-from-dr-bradley-schuster.php/. 2 pages.

Schwartz, Enhancing Glaucoma Patients' Adherence to Prescribed Medical Therapy. Glaucoma Today. Jul./Aug. 2014 39-43.

Strouthidis, Trabeculectomy. 2014. Available at ngsglaucoma.com/glaucomatrab.html 1 page.

Tham et al., Global prevalence of glaucoma and projections of glaucoma burden through 2040: a systematic review and meta-analysis. Ophthalmology. Nov. 2014;121(11):2081-90. doi: 10.1016/j.ophtha.2014.05.013. Epub Jun. 26, 2014.

Thomas et al., How to assess a patient for glaucoma. Community Eye Health. Sep. 2006;19(59):36-7.

Tsai, High Eye Pressure and Glaucoma. Glaucoma Research Foundation. Oct. 29, 2017. Available at glaucoma.org/gleams/high-eye-pressure-and-glaucoma.php. 2 pages.

International Search Report and Written Opinion dated Sep. 18, 2018 for Application No. PCT/US2018/037764.

International Preliminary Report on Patentability dated Dec. 26, 2019 for Application No. PCT/US2018/037764.

* cited by examiner

MODULAR GLAUCOMA IMPLANT

RELATED APPLICATIONS

This application is a national stage filing under 35 U.S.C. § 371 of International PCT application, PCT/US2018/037764, filed Jun. 15, 2018, which claims the benefit of priority under 35 U.S.C. § 119(e) to U.S. Provisional Application Ser. No. 62/520,647, filed Jun. 16, 2017, the contents of each of which is incorporated herein by reference in its entirety for all purposes.

FIELD

Disclosed embodiments are related to glaucoma treatment devices.

BACKGROUND

Glaucoma is a disease that arises when the optic nerve in the eye becomes damaged, leading to vision loss. The damage that occurs to the optic nerve is often, but not always, associated with elevated intraocular pressure (IOP) due to poor drainage of the aqueous humor from the anterior chamber of the eye.

A certain level of IOP is necessary to inflate the eye and maintain the proper shape and optical properties of the globe of the eye. The primary fluid of the eye which helps maintain its shape-aqueous humor, is produced within the ciliary body of the eye and actively secreted into the posterior chamber of the eye before entering the anterior chamber—the region between the iris and the cornea. From there, the humor flows passively out of the eye via two pathways originating at the limbus. In the primary outflow pathway, aqueous humor passes through the trabecular meshwork (TM) and enters the Schlemm's Canal, where it collects in drainage channels before finally entering the neighboring vascular network for removal. In the secondary outflow pathway, aqueous humor enters the connective tissue around the ciliary muscles, passes into the suprachoroidal space, and then into the neighboring vascular network for removal. In a healthy patient, approximately 70% of aqueous humor drainage occurs via the primary outflow pathway, with the remaining approximately 30% occurring via the secondary outflow pathway.

When the outflow of aqueous humor is abnormally impeded, it can build up within the anterior chamber and cause an increase in IOP. High IOP can cause damage to, and deformation of, the optic nerve directly causing loss of vision and potential blindness.

SUMMARY

In some embodiments a device for implanting into an eye is provided. The device comprises a curved fixation stent having a first end and a second end separated by the length of the fixation stent, the fixation stent including one or more through holes across a width of the fixation stent from a first side to a second side of the fixation stent; and a first drainage tube with a first end and a second end, constructed and arranged to be insertable into one of the one or more through holes in the fixation stent. A first fluid flow path for fluid to enter or exit the device exists between the first and second ends of the fixation stent. The method involves inserting the first drainage tube into the fixation stent creates a second flow path transverse to the first flow path.

In some embodiments a method of diverting fluid in an eye is provided. The method comprises inserting a first end of a curved fixation stent into a fluid source, and a second end of the fixation stent into a first fluid sink to establish a first fluid flow path through the fixation stent, wherein the fixation stent comprises one or more through holes across a width of the fixation stent from a first side to a second side of the fixation stent; and inserting a first drainage tube into one of the one or more through holes such that a first end of the first drainage tube protrudes from the first side of the fixation stent, and a second end of the first drainage tube protrudes from the second side of the fixation stent, wherein the first end of the first drainage tube connects to the fluid source and the second end of the first drainage tube connects to a second fluid sink, establishing a second fluid flow path transverse to the first fluid flow path.

In some embodiments a device for implanting into an eye is provided. The device comprises a curved fixation stent having a first end and a second end across a length of the fixation stent, and a first side and a second side across a width of the fixation stent; a first drainage tube having a first end and second end, constructed and arranged such that a first end of the first drainage tube extends from the first side of the fixation stent, and the second end of the first drainage tube extends from the second side of the fixation stent.

In some embodiments a method of diverting fluid in an eye is provided. The method comprises flowing fluid from a fluid source through a curved fixation stent from a first end to a second end of the fixation stent so as to establish a first fluid flow path through the fixation stent, wherein the fixation stent has a width from a first side to a second side of the fixation stent, and wherein the fixation stent comprises a first drainage tube having a first end that protrudes from the first side of the fixation stent, and a second end of the first drainage tube protrudes from the second side of the fixation stent; and flowing fluid from the fluid source through at least a portion of the first drainage tube, so as to establish a second fluid flow path transverse to the first flow path.

In some embodiments, an implantable glaucoma drainage device comprising an intracanalicular fixation stent is provided. The device comprises at least one suprachoroid drainage tube in fluid communication with the fixation stent. The fixation stent and the at least one drainage tube may be made of a non-metallic, hydrophobic, non-porous material. A radius of curvature of the fixation stent matches that of the Schlemm's Canal in an eye. The fixation stent may include at least one hole for receiving a drainage tube for fluid communication. The curvature of the drainage tube may match the curvature of the corneal-scleral juncture. The fixation stent may include retention rings for fixation in the Schlemm's Canal.

While in some embodiments the fixation stent is made from a non-metallic, hydrophobic, non-porous material, embodiments made of metals and/or porous materials (e.g., porous polymers) are also possible.

In some embodiments involving the devices and/or methods described herein, the first drainage tube is inserted into the fixation stent, the first end of the drainage tube extends from the first side of the fixation stent, and the second end of the drainage tube extends from the second side of the fixation stent.

In some embodiments involving the devices and/or methods described herein, the fixation stent comprises one or more through-holes along the width of the fixation stent.

In some embodiments involving the devices and/or methods described herein, the device is constructed and arranged to facilitate fluid flow through a first flow path through the fixation stent from the first end of the fixation stent to the second end of the fixation stent.

In some embodiments involving the devices and/or methods described herein, the device further comprising a second drainage tube, constructed and arranged such that a first end of the second drainage tube extends from the first side of the fixation stent, and the second end of the second drainage tube extends from the second side of the fixation stent.

In some embodiments involving the devices and/or methods described herein, the device further comprises a third drainage tube, constructed and arranged such that a first end of the third drainage tube extends from the first side of the fixation stent, and the second end of the third drainage tube extends from the second side of the fixation stent.

In some embodiments involving the devices and/or methods described herein, the fixation stent is constructed and arranged include a second flow path, transverse to the first flow path, through the first drainage tube.

In some embodiments involving the devices and/or methods described herein, the first drainage tubes are curved about different axes than the respective fixation stents.

In some embodiments involving the devices and/or methods described herein, the first drainage tubes comprise bulges in between their respective first and second ends.

In some embodiments involving the devices and/or methods described herein, the first drainage tube snap-fits with the through-holes of the fixation stents.

In some embodiments involving the devices and/or methods described herein, the first drainage tubes are removable from the fixation stents.

In some embodiments involving the devices and/or methods described herein, the first drainage tubes comprise through-holes in the bulges, allowing flow from the first end to the second end of the fixation stents.

In some embodiments involving the devices and/or methods described herein, the first drainage tubes comprise a plurality of fenestrations at their second ends.

In some embodiments involving the devices and/or methods described herein, the device further comprising retention rings extending substantially circumferentially from the first ends of the fixation stents.

In some embodiments involving the devices and/or methods described herein, the fixation stents are made of a biocompatible material comprising one or more of: polyimide, silicone, Teflon, polypropylene, perfluoroalkoxy, fluorinated ethylene-propylene, carbothane, polyurethanes, polyethylenes, acrylic, collamer, nylon, nitinol, stainless steel, tantalum, gold, titanium, or platinum.

In some embodiments involving the devices and/or methods described herein, the device comprises a coating layer comprising one or more of: albumin, rapamycin, polyethylene glycol, tacrolimus, an anti-fibrotic drug, an anti-fouling agent, or fibronectin.

In some embodiments involving the devices and/or methods described herein, the first drainage tube comprises a transverse through-hole between the first and second ends of the first drainage tube, allowing a second flow path through the first drainage tube and the first flow path through the fixation stent to merge.

In some embodiments involving the devices and/or methods described herein, the fixation stent is constructed and arranged to include a third flow path, transverse to the first flow path, through a second drainage tube.

In some embodiments involving the devices and/or methods described herein, the fixation stent has a length of between 5 mm and 20 mm.

In some embodiments involving the devices and/or methods described herein, the drainage tubes have a length of between 1 mm and 10 mm.

In some embodiments involving the methods described herein, the method comprises inserting a second drainage tube into one of the one or more through-holes such that a first end of the second drainage tube protrudes from the first side of the fixation stent, and a second end of the second drainage tube protrudes from the second side of the fixation stent, wherein the first end of the second drainage tube connects to the fluid source and the second end of the second drainage tube connects to a second fluid sink, establishing a third fluid flow path transverse to the first fluid flow path.

In some embodiments involving the methods described herein, the method comprises inserting a third drainage tube into one of the one or more through-holes such that a first end of the third drainage tube protrudes from the first side of the fixation stent, and a second end of the third drainage tube protrudes from the second side of the fixation stent, wherein the first end of the third drainage tube connects to the fluid source and the second end of the third drainage tube connects to a second fluid sink, establishing a fourth fluid flow path transverse to the first fluid flow path.

In some embodiments involving the methods described herein, the second flow path also fluidly connects to the second fluid sink through a plurality of fenestrations in the second end of the first drainage tube.

In some embodiments involving the methods described herein, the first drainage tube includes a through-hole between the first and second ends of the first drainage tube such that the first and second flow paths merge within the fixation stent, such that fluid flows from the fluid source to a first fluid sink across at least a portion of the second flow path, and from the fluid source to a second fluid sink across at least a portion of the first flow path.

In some embodiments involving the methods described herein, the method comprises flowing fluid from the fluid source through at least a portion of a second drainage tube, having a first end that protrudes from the first side of the fixation stent, and a second end of the second drainage tube protrudes from the second side of the fixation stent, such that fluid flows through the second drainage tube so as to establish a third fluid flow path transverse to the first flow path, and fluid flows from the fluid source to the second fluid sink across at least a portion of the third flow path.

In some embodiments involving the method described herein, the method comprises flowing fluid from the fluid source through at least a portion of a third drainage tube, having a first end that protrudes from the first side of the fixation stent, and a second end of the third drainage tube protrudes from the second side of the fixation stent, such that fluid flows through the third drainage tube so as to establish a fourth fluid flow path transverse to the first flow path, and fluid flows from the fluid source to the second fluid sink across at least a portion of the fourth flow path.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Glaucoma is often managed with surgical procedures like the trabeculectomy, or through implantable drainage devices, for example, minimally invasive glaucoma surgery (MIGS) devices.

A trabeculectomy is a surgical procedure, during which a surgeon cuts through the corneal-scleral region of the eye to create a pathway for fluid to drain from the anterior chamber into a bleb on the conjunctiva in the outer portion of the eye. This surgery can be effective in the long term, but there are a variety of disadvantages to the procedure. Trabeculectomies are fairly invasive, requiring a skilled surgeon and taking on average 45-90 minutes of surgical time. Additionally, the amount of aqueous humor outflow needed to maintain the correct level of TOP varies significantly by patient. As a result, even a trained surgeon cannot guarantee the correct amount of flow in an initial procedure, thus potentially requiring a secondary corrective procedure to increase or decrease the flow rate of aqueous humor out of the anterior chamber. Finally, trabeculectomies often result in scarring on the eye, decreasing the efficacy of the treatment.

Minimally Invasive Glaucoma Surgery (MIGS) Devices are commonly stents that can be implanted at least partially in the anterior chamber of the eye to connect the anterior chamber either through the TM to the Schlemm's Canal, or further through the sclera to the suprachoroidal space. Due to the difference in anatomical locations of Schlemm's Canal and the suprachoroidal space relative to the anterior chamber, MIGS devices known in the art only connect to one structure or the other. Some MIGS currently known in the art can be implanted relatively quickly in comparison to a trabeculectomy procedure, in as few as 5-10 minutes. However, some of the devices currently known in the art are notoriously insecure in their optimal implanted locations, frequently becoming dislodged and requiring corrective procedures to fix. Additionally, due to the size constraints of the environment, MIGS have particularly small diameters in order to fit. As a result, they tend to enable only relatively low flow rates out of the anterior chamber, and are furthermore easily clogged by proteins and other solids naturally present in the aqueous humor. When such devices become clogged, further surgery is also required to reestablish function of the devices.

Bearing in mind at least the issues of long implantation time, low flow rate, inflexible flow rate control, and consistency of fixation so common among various existing devices and surgical procedures: the inventors have contemplated that implantable glaucoma treatment devices could be improved.

According to one embodiment of the modular glaucoma implant, the device includes an elongate fixation stent that is implanted primarily in the Schlemm's Canal such that an inflow end of the device protrudes anterior-medially into, and rests partially in, the anterior chamber, allowing aqueous humor to freely enter the inflow end of the fixation stent and drain into the Schlemm's Canal. The device further includes a plurality of drainage tubes, which can be optionally inserted into through-holes of the fixation stent such that they protrude from either side of the fixation stent and rest substantially perpendicularly to the length of the fixation stent. The fixation stent and drainage tubes are curved in such a manner that when the drainage tubes are inserted into the fixation stent, the opposing ends of the drainage tube extend posterior-medially into the anterior chamber and posterior-laterally into the suprachoroidal space respectively. Aqueous humor is free to flow from the anterior chamber through at least one drainage tube to the suprachoroidal space.

As should be readily appreciated, the design of the modular glaucoma implant allows aqueous humor to flow from the anterior chamber to both the Schlemm's Canal through one flow path, and from the anterior chamber to the suprachoroidal space through flow paths created when one or more drainage tubes are inserted. The more drainage tubes inserted, the more flow paths for aqueous humor to leave the eye. The modularity of the device allows a surgeon to tailor the device to the desired rate of aqueous humor outflow from the anterior chamber during implantation. By opting to add an additional drainage tube, a surgeon can increase the flow rate without the need of implanting a larger stent or performing a second corrective procedure as would be needed with currently known devices and procedures.

Without the need to rely on using a stent of larger diameter to increase the flow rate, the fixation stent and drainage tubes can be small enough in some embodiments to be implanted while requiring only minimally invasive implantation procedures, e.g. through a clear-corneal incision that does not need stitching to close. The small size may allow the modular glaucoma implant to be implanted in quick minimally invasive procedures requiring 5-15 minutes, matching certain existing devices known in the art.

A further advantage of the modular arrangement is that additional flow paths also serve as redundant flow paths if one or more flow paths becomes blocked. In certain existing devices, when a blockage occurs, corrective surgical procedures are required to immediately rectify the issue to prevent the buildup of IOP. With additional flow paths to allow aqueous humor to continue exiting the anterior chamber despite the blockage, the continued outflow from the anterior chamber facilitatable by the current device prevents TOP from rapidly building up, leading to continued damage.

In some embodiments of the modular glaucoma implant, the drainage tubes further include through-holes that go through one lateral side of the drainage tube to the other. In these embodiments, when the drainage tubes are inserted into the fixation stent, the through-holes of the drainage tubes align with the flow path of aqueous humor through the fixation stent. As a result, the flow paths through the drainage tubes transverse to the flow paths through the fixation stent intermix together, allowing aqueous humor that entered the fixation stent to mix with aqueous humor that entered a drainage tube and exit to either the suprachoroidal space or the Schlemm's Canal, increasing the flow rate of aqueous humor exiting the anterior chamber.

Due to the relative anatomical locations of the Schlemm's Canal, anterior chamber, and the suprachoroidal space, the fixation stent and the drainage tubes protrude in different directions. Phrased another way, when drainage tubes are inserted, lateral projections extend from the length of the fixation stent. One consequence of this arrangement is that when the device is implanted, the fixation stent and drainage tubes may protrude through different sections of tissue. The fixation stent may extend through the trabecular meshwork and along the Schlemm's Canal, while the drainage tubes may extend in a different direction through the sclera. Thus, assuming proper implantation, the device may become anchored in different sections of tissue and further has lateral projections interrupting elongate sections. As a result, without wishing to be bound by theory, the device has advantages in fixation over certain existing devices because the device described herein resist dislodgment upon impact or natural movement by virtue of redundant anchoring in different locations, and further has lateral projections that prevent sliding in the elongate direction. This arrangement further produces an additional advantage of not requiring sutures to stabilize the implant during implantation.

In some embodiments, the drainage tubes snap-fit into the fixation stent, where the snap-fit features of the drainage tubes further prevent dislodgment of the drainage tubes from the fixation stent.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

Figure 1:
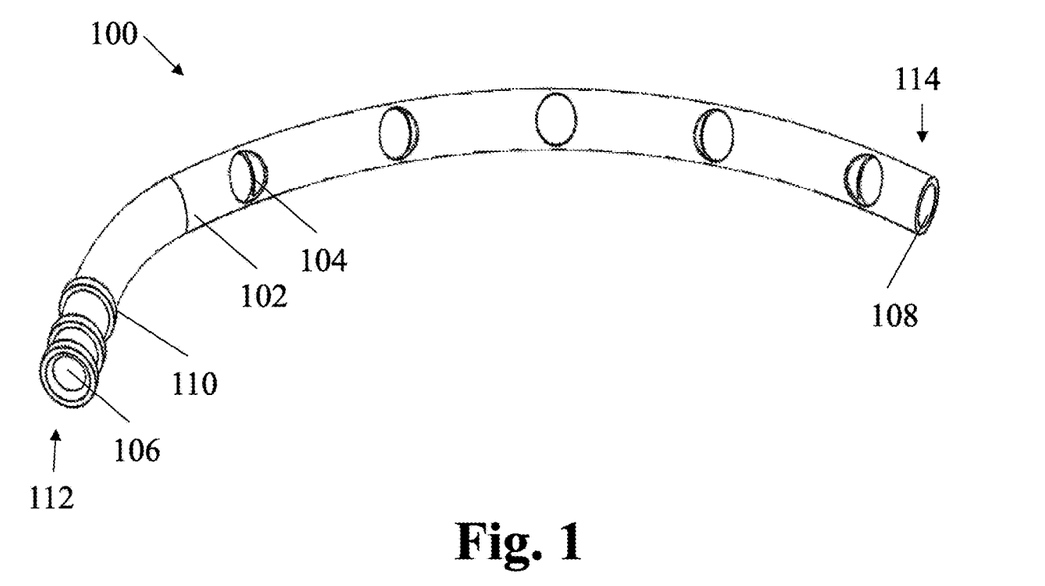
FIG. 1 is a top, front, right, perspective view of a fixation stent according to one embodiment of the modular glaucoma implant.

FIG. 1 shows a fixation stent 100 according to one embodiment of the modular glaucoma implant. A stent body 102 includes a plurality of through-holes 104 that go from one lateral side of the device (e.g. a first side, a second side) to the other lateral side (e.g. a second side, a first side) spaced across a width of the fixation stent from a first side to a second side of the fixation stent. Longitudinal ends of the stent body are marked by inflow end 112 (e.g., a first end, a second end) that receives aqueous humor (e.g. a fluid) from the anterior chamber (e.g. a fluid source) through inflow aperture 106, and outflow end 114 (e.g., a second end, a first end) that may output at least some of the aqueous humor through outflow aperture 108. Inflow end 112 to outflow end 114 are arranged such that a first fluid flow path for fluid to enter or exit the device exists between the first and second ends of the fixation stent. Optional retention rings 110 at the inflow end 112 of stent body 102 may both aid in the fixation of the fixation stent and provide visual feedback for the correct insertion depth during implantation.

Figure 2:
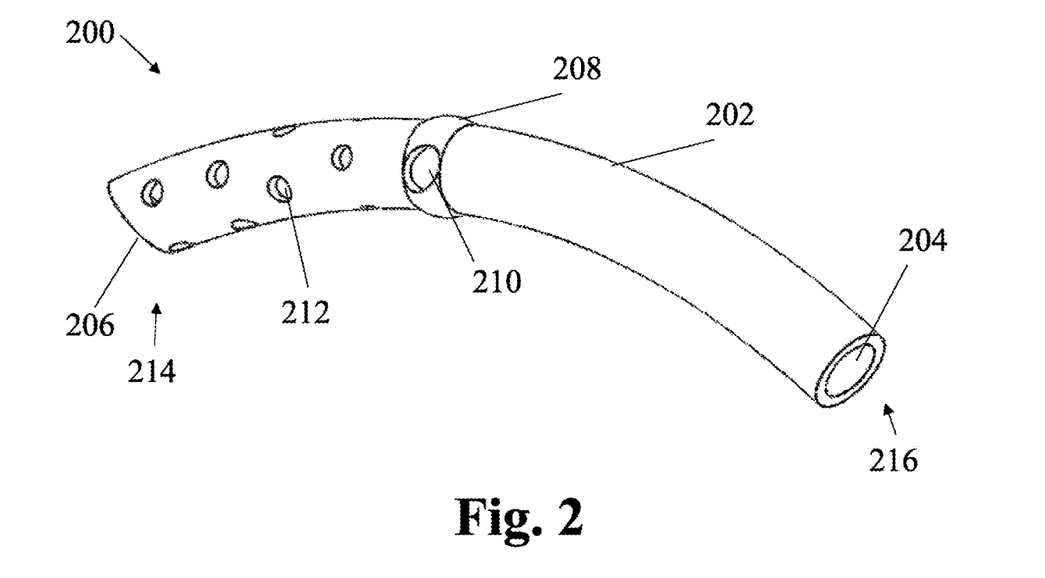
FIG. 2 is a top, front, left, perspective view of a drainage tube according to one embodiment of the modular glaucoma implant.

FIG. 2 shows a drainage tube 200 according to one embodiment of the modular glaucoma implant. A tube body 202 includes an inflow end 216 (e.g. a first end of the drainage tube, a second end of the drainage tube) that receives aqueous humor from the anterior chamber (e.g. a fluid source) through inflow aperture 204, and an outflow end 214 (e.g. a second end of the drainage tube, a first end of the drainage tube) that outputs the aqueous humor through fenestrations 212 or outflow aperture 206. As shown illustratively in this figure, the tube body 202 includes an optional bulge 208 with through-hole 210 extending from one lateral side of the drainage tube to the other lateral side through bulge 208.

Figure 3A:
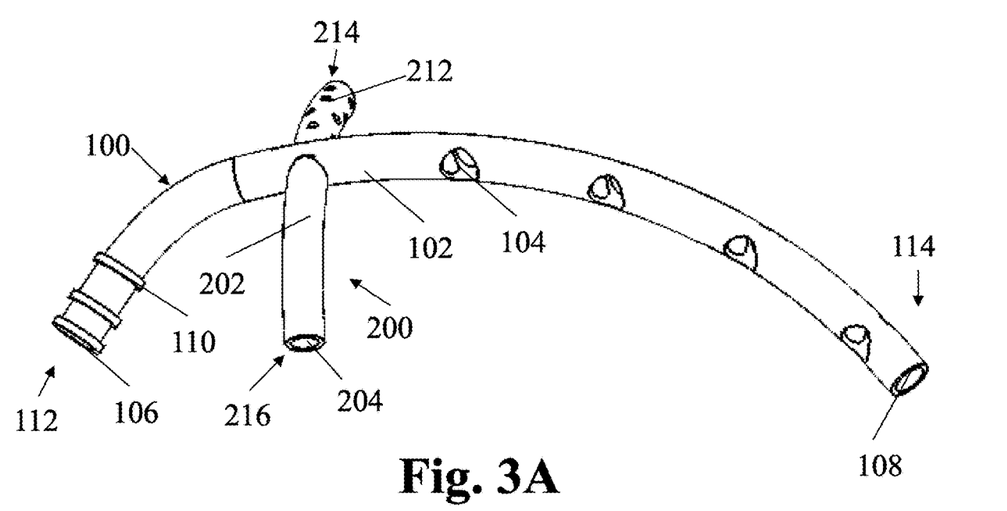
FIG. 3A is a top, front, right, perspective view of one configuration of the modular glaucoma implant according to one embodiment.
Figure 3B:
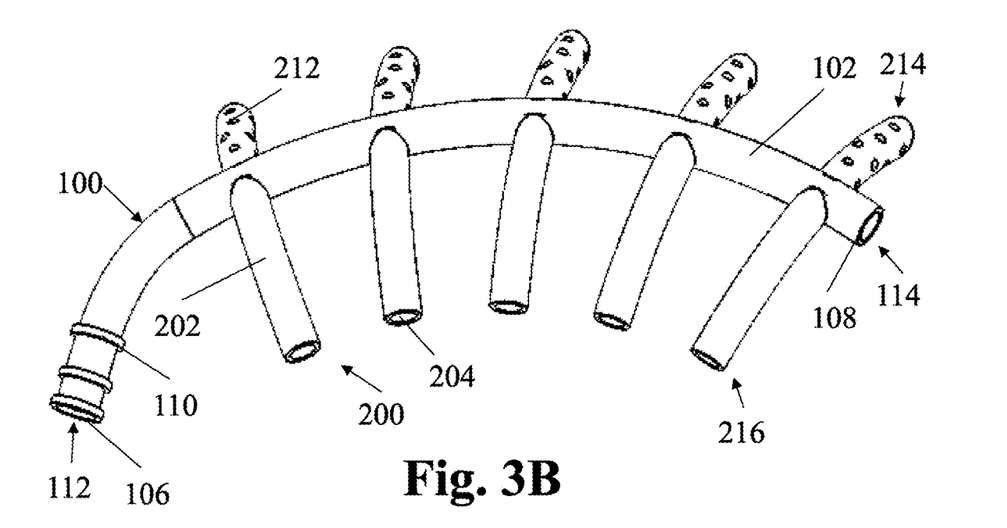
FIG. 3B is a top, front, right, perspective view of another configuration of the modular glaucoma implant according to the embodiment of FIG. 3A.

FIGS. 3A and 3B show the fixation stent 100 with one or more drainage tubes 200 inserted into the fixation stent. In practice, in this embodiment of the modular glaucoma implant, the drainage tubes are constructed and arranged to be insertable into one of the one or more through-holes of the fixation stent such that a first end of each drainage tube protrudes from the first side of the fixation stent, and a second end of each drainage tube protrudes from the second side of the fixation stent. A surgeon can insert a drainage tube into through-holes 104 until bulge 208 enters the fixation stent 100. The bulge 208 of the drainage tube 200 creates a snap-fit with the fixation stent 100, preventing the drainage tube from being pushed through the fixation stent 100, and further preventing the drainage tube 200 from easily being removed from fixation stent 100. When inserted, the inflow end 216 of the drainage tube extends from one lateral side of fixation stent 100, while outflow end 214 of the drainage tube extends from the other lateral side of fixation stent 100. While configurations with one tube and five tubes are depicted, it should be understood that any suitable number of drainage tubes, in any order of insertion, occupying any of the through-holes 104 in any suitable pattern are also possible. Each additional drainage tube inserted into the fixation stent creates an additional (e.g. a second, third, fourth . . . flow path), transverse to the first flow path, leading from the inflow end to the outflow end of each inserted drainage tube.

Figure 4:
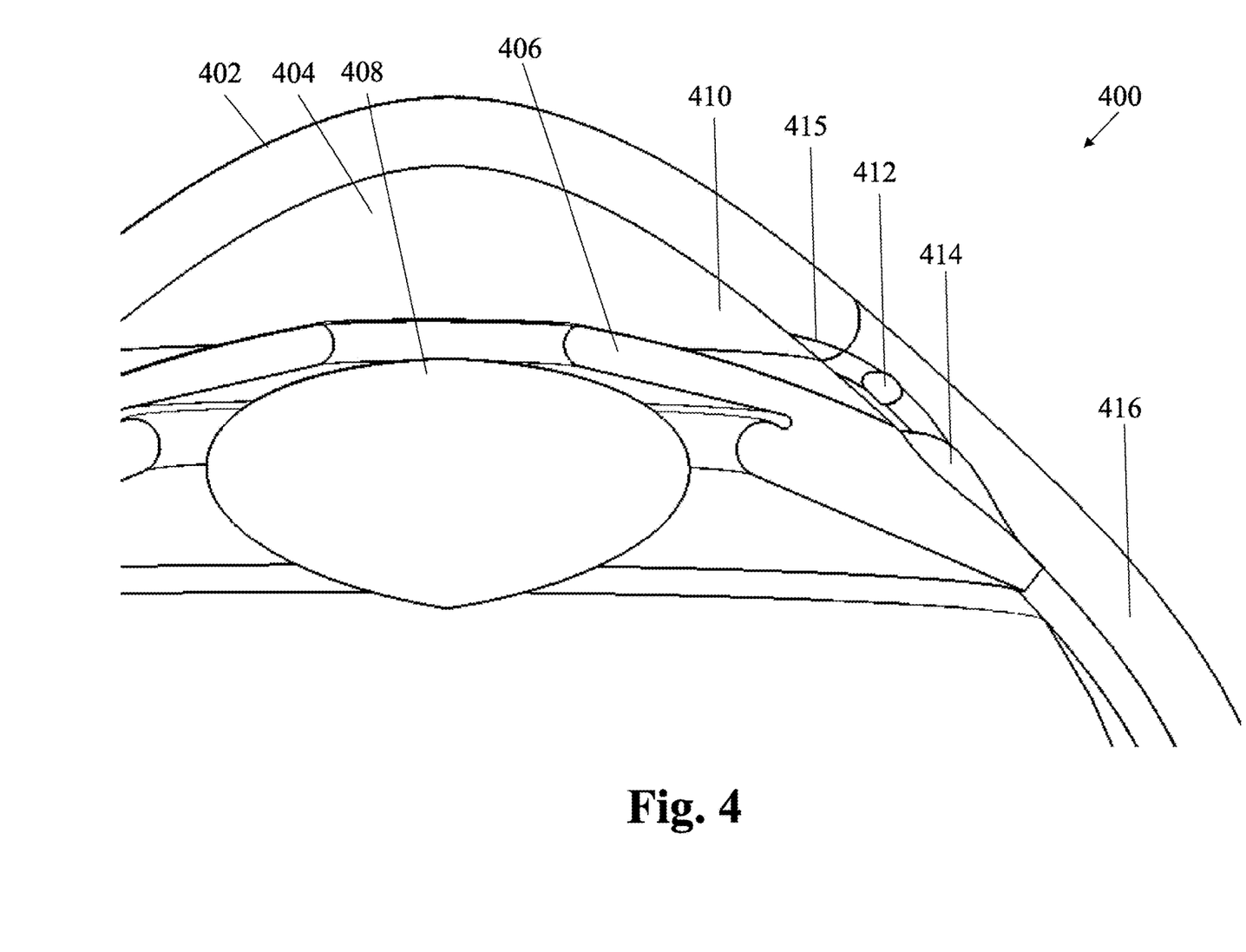
FIG. 4 is a partial, schematic, cross-sectional view of a representative human eye.
Figure 5:
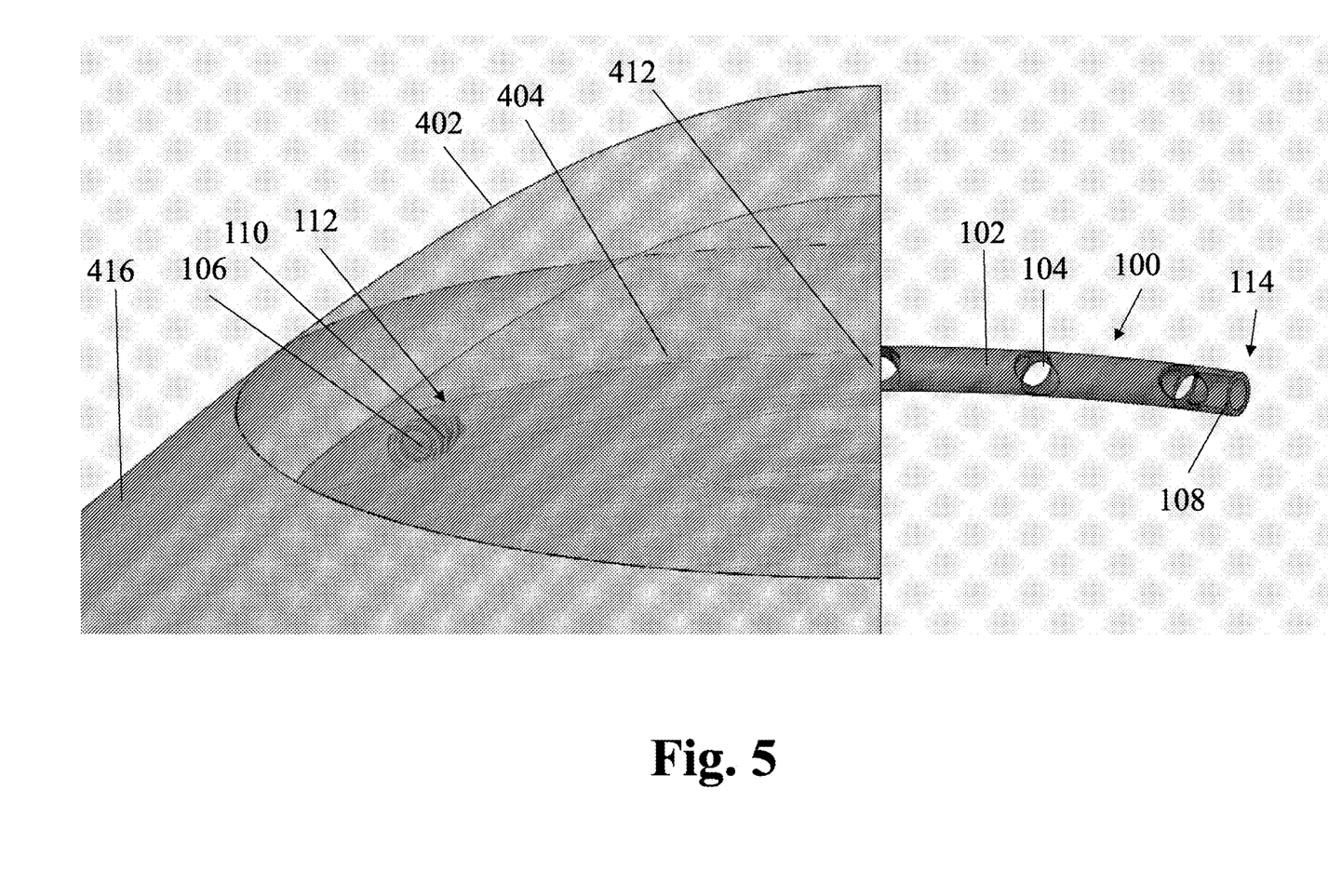
FIG. 5 is a top, front, right, perspective view of a fixation stent according to one embodiment implanted in a representative eye shown in cutaway.
Figure 6:
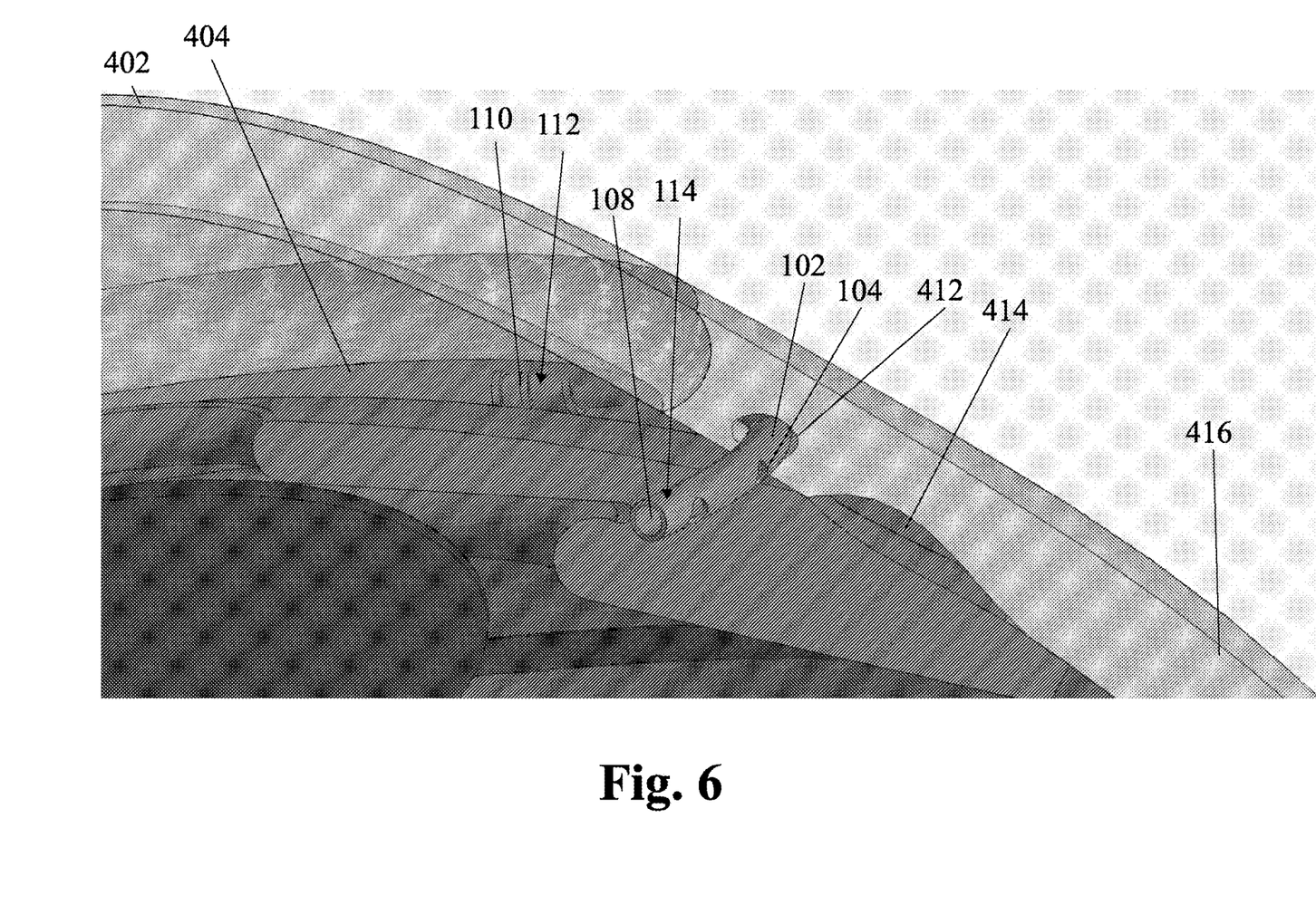
FIG. 6 is a top, rear, left, perspective view of the fixation stent of FIG. 5 implanted in a representative eye shown in cutaway.

FIG. 4 shows a schematic representation of the relevant structures of the human eye 400. It should be understood that anatomical structures depicted in this figure and in subsequent figures form no part of the described device and are merely shown to facilitate understanding. The anterior chamber 404 rests between the cornea 402 and iris 406. After production in the ciliary body (not depicted), aqueous humor flows from behind the iris 406 to enter the anterior chamber 404. Schlemm's Canal 412 extends perpendicularly into and out of the page relative to the cross-section of FIG. 4. Suprachoroidal space 414 is separated from anterior chamber the angle 410 of the anterior chamber 404 by sclera 416. Channel 415 is not a naturally occurring structure and is merely illustrative of where a drainage tube will rest in the sclera when implanted.

As shown illustratively in FIGS. 5-8, fixation stent 100 rests primarily along Schlemm's Canal 412 (e.g. a first fluid sink), and is sized and curved to match the natural shape of the canal and the curvature of the eye. When implanted, inflow end 112 extends into the angle 410 of the anterior chamber 404. When implanted properly, at least one of retention rings 110 should remain in the anterior chamber 404. Outflow aperture 108 and through-holes 104, when not occupied, fluidly connect aqueous humor from anterior chamber 404 to Schlemm's Canal 412, where the aqueous humor can eventually move to the neighboring vascular network for processing.

Figure 7A:
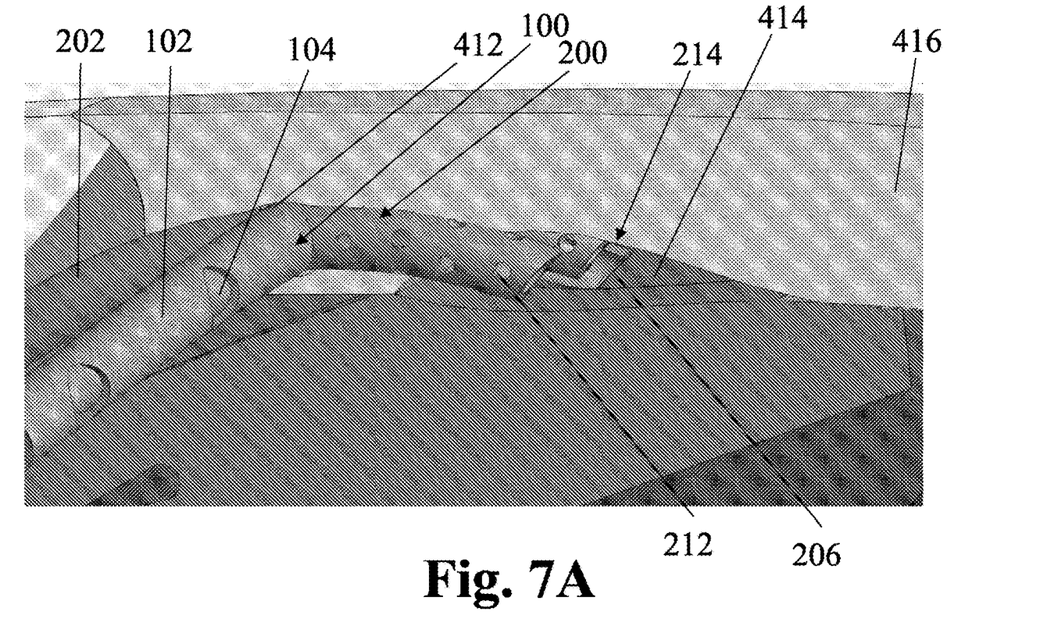
FIG. 7A is a close-up, top, rear, left, perspective view of another configuration of the modular glaucoma implant of FIGS. 3A and 3B implanted in a representative eye shown in cutaway.
Figure 7B:
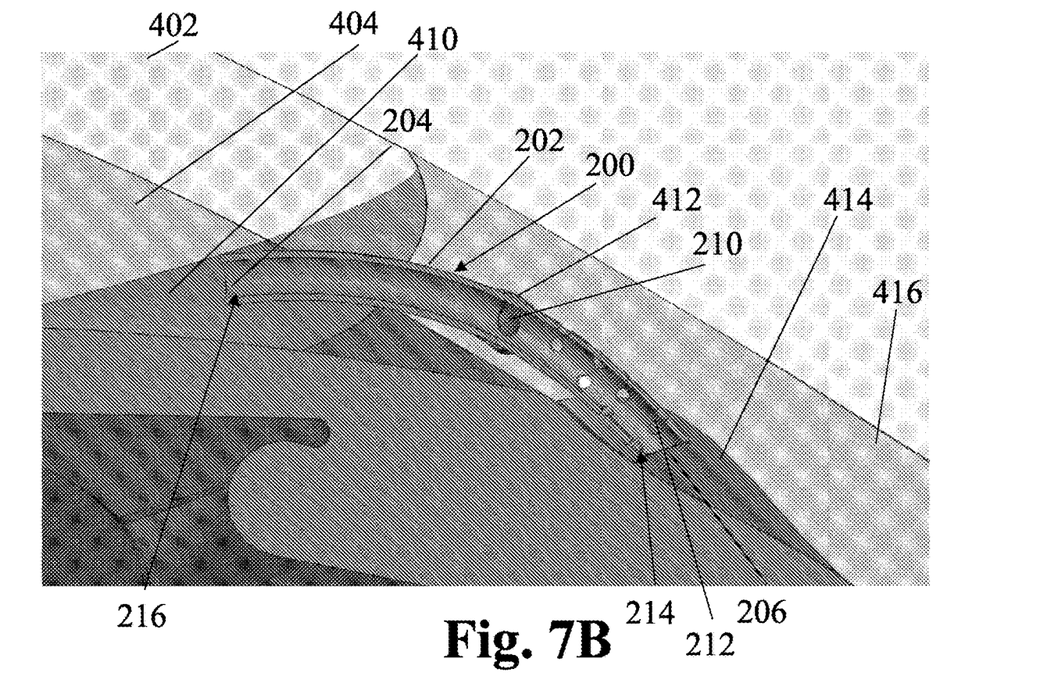
FIG. 7B is a close-up, rear, left, cross-sectional view of the modular glaucoma implant of FIG. 7A implanted in a representative eye shown in cutaway.
Figure 8:
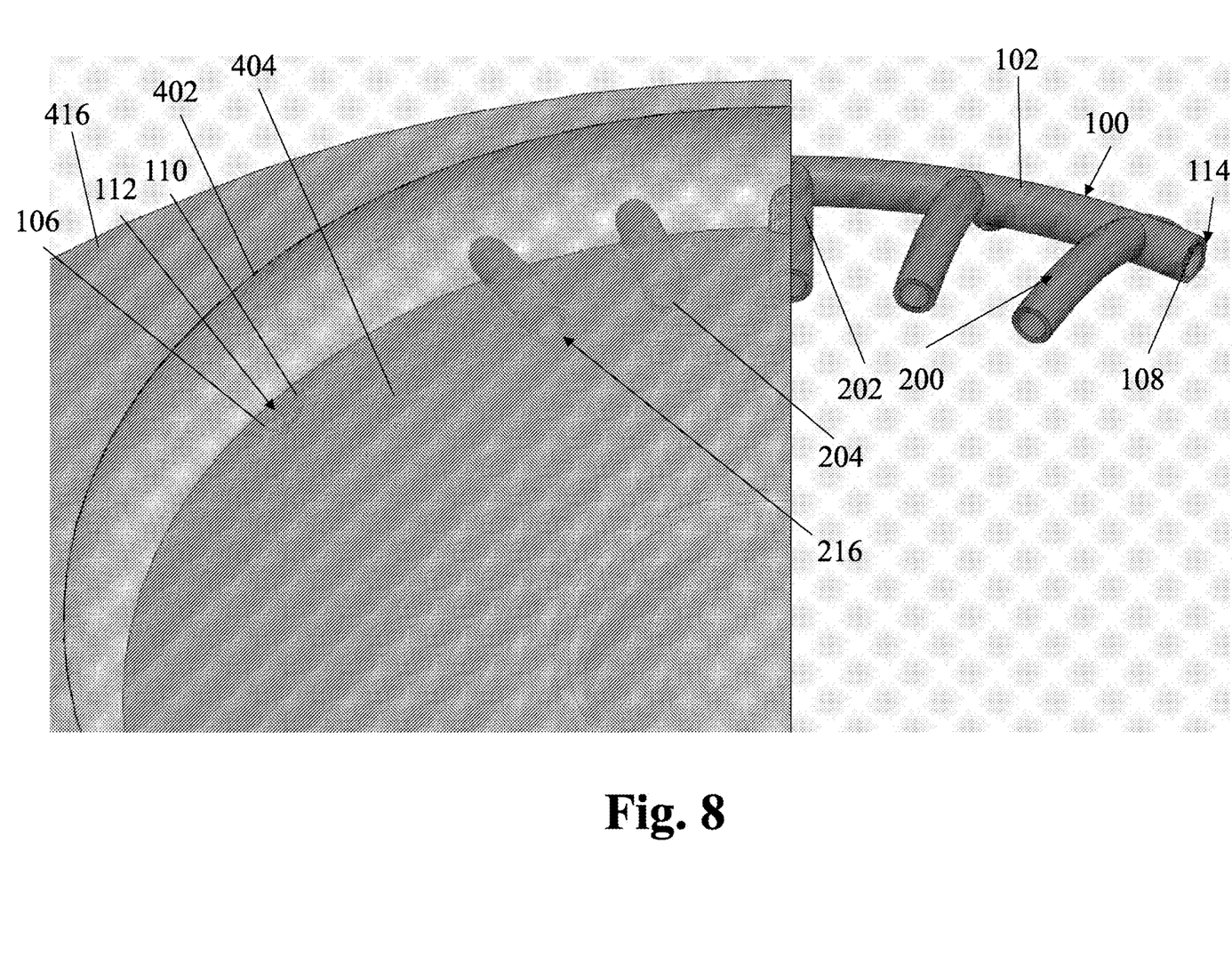
FIG. 8 is a top, right, perspective view of the modular glaucoma implant of FIG. 7A implanted in a representative eye shown in cutaway.

As shown illustratively in FIGS. 7A, 7B, and 8, when one or more drainage tubes 200 are inserted, the drainage tubes extend from the angle 410 of the anterior chamber 404, through the sclera, perpendicularly through fixation stent 100, to the suprachoroidal space 414. The drainage tubes 200 are curved in a different direction than fixation stent 100 to match the curvature of the corneal-scleral juncture. Aqueous humor moving through the drainage tubes begin in the anterior chamber 404 and can exit the drainage tube in the suprachoroidal space 414 through outflow aperture 206 or fenestrations 212. In embodiments including through-hole 210 in the drainage tubes, aqueous humor that entered the inflow end of a drainage tube can end up in the Schlemm's Canal due to the mingling of the flow paths through the fixation stent and through the drainage tube. Similarly, aqueous humor that entered the inflow end of the fixation stent could exit to the suprachoroidal space (e.g. a second fluid sink).

In practice, a surgeon can implant the modular glaucoma implant as follows. However, it should be recognized that surgeons can vary in technique and preference and the specifics of surgical implantation are ever changing and improving. The following intends only to guide one of skill in the art in the general use of the device and is not intended to be a limiting explanation of the process. For example, guidelines for surgical incisions or suggested insertion depths of parts of the modular glaucoma implant can be varied based on the patient's circumstances or the surgeon's preferences. Similarly, the specific surgical tools used can be varied based on preference or the state of technology.

The fixation stent can be first inserted into the Schlemm's Canal with a curved cannula inserted through a lateral clear corneal incision. The tip of the cannula could be used to incise the inner wall of the trabecular meshwork, just above the scleral spur, to open a channel for the fixation stent to be inserted through the trabecular network and into the Schlemm's Canal. Depending on the embodiment, the fixation stent should be inserted into the Schlemm's Canal until approximately 1-2 mm of stent is left protruding from the trabecular meshwork, leaving at least one retention ring visible in the anterior chamber.

After insertion of the fixation stent, a surgeon could then insert one or more drainage tubes if desired. The drainage tubes could be inserted in the same procedure, or in a subsequent procedure if desired or if necessary. Drainage tubes can be inserted one at a time with the aid of a retractable curved guide needle through a second clear corneal incision approximately 90 degrees proximal to the original incision for inserting the fixation stent. The curved guide needle is first inserted radially into the trabecular meshwork, passing through one of the through-holes of the fixation stent, cutting a channel through the sclera, and entering the suprachoroidal space. The drainage tube can then be advanced down the guide needle until the bulge of the drainage tube snaps into the fixation stent. In some embodiments, the outflow end of the drainage tube should be in the suprachoroidal space, with the inflow end of the drainage tube extending safely into the anterior chamber. The same clear corneal incision can be used for the insertion of further drainage tubes. As mentioned, further procedures can be performed at any time to either add or plug extra drainage tubes to allow for flow adjustment.

In some embodiments of the fixation stent, the fixation stent is an elongate hollow tube curved to match the curvature of the Schlemm's Canal with through-holes equally spaced along the length of the stent body. It should be understood however that the current application is not limited as such. For instance, embodiments are contemplated where the fixation stent includes two or more channels that extend the length of the stent body. Embodiments where the fixation stent is merely a curved cylinder with through-holes for drainage tubes are possible as well. The fixation stent also is not limited to being circular in cross-section, and could have cross-sections of any shape.

While the depicted drainage tubes have five through-holes, any suitable number of through-holes may be possible. For example, a drainage tube may include at least 1, at least 2, at least 3, at least 4, at least 5, at least 6, at least 7, at least 8, at 9, at least 10 through-holes. In some embodiments, the drainage tube may include less than or equal to 15, less than or equal to 12, less than or equal to 10, less than or equal to 8, less than or equal to 6, or less than or equal to 4 through-holes. Combinations of the above-referenced ranges are also possible. Other ranges are also possible.

Moreover, a drainage tube may be of any suitable size, of any suitable shape, sized consistently or inconsistently, spaced consistently or inconsistently, and/or of any suitable distance apart when connected to a fixation stent. In some embodiments, the fixation stent includes holes on either lateral side of the stent body that do not necessarily align and two halves of drainage tubes are attached to each hole to allow aqueous humor to flow laterally through the fixation stent.

While depicted embodiments show fixation stents with three retention rings spaced equally apart, it should be understood that any number of retention rings spaced consistently or inconsistently apart are also contemplated. In some embodiments, the retention rings have different diameters. For example, one or more of the retention rings could be of larger diameter than the others to ensure that a surgeon does not implant the fixation stent beyond the larger retention rings. Embodiments without retention rings are also contemplated.

In some embodiments of the drainage tubes, the drainage tubes are elongate hollow tubes curved to match the curvature of the corneal-scleral junction with a bulge substantially in the center of the drainage tube with through-holes in the bulge to allow flow paths of the fixation stent and the drainage tubes to merge. As should be understood by those of skill in the art, without wishing to be bound by theory, to match their respective anatomical target locations, the fixation stent and drainage tubes are curved about different axes. It should be understood that the current disclosure is not limited as such. For example, embodiments are contemplated where the drainage tubes are solid curved cylinders with two or more channels that extend longitudinally through the cylinder. The drainage tubes also are not limited to being circular in cross-section, and could have cross-sections of any shape. In some embodiments, drainage tubes are inconsistent or variable in shape and configuration from drainage tube to drainage tube.

While the depicted embodiments have 16 fenestrations in the outflow end of the drainage tubes, any number of fenestrations or no fenestrations at all are contemplated. For example, a drainage tube may include at least 1, at least 2, at least 4, at least 6, at least 8, at least 10, at least 12, at least 16, at 18, at least 20 fenestrations. In some embodiments, the drainage tube may include less than or equal to 30, less than or equal to 25, less than or equal to 20, less than or equal to 15, less than or equal to 10, or less than or equal to 5 fenestrations. Combinations of the above-referenced ranges are also possible. Other ranges are also possible.

The fenestrations may be shaped, sized, spaced, in any suitable manner, consistently or inconsistently. Similarly, more than one through-hole of any suitable shape, size, or arrangement may be possible. Embodiments with no through-holes and bulges large enough to prevent dislodging of the drainage tube, but small enough to aqueous humor to flow around the bulge within the fixation stent are possible. The bulges can be of any suitable diameter, and do not have to bulge consistently all around the drainage tube. Other snap-fit arrangements are considered; for example, the center of the drainage tube may include a pair of flanges that are just larger in diameter than the corresponding through-holes of the fixation stent such that the flanges can elastically deform just enough to maintain the insertion.

Other mechanisms of attaching the drainage tubes to the fixation stent are also possible. The current application is not limited to snap-fitting. For example, the center of the drainage tubes may be pre-treated with a bio-compatible adhesive such that the tube body sticks in place after insertion. The tube body may be threaded to match threading in the through-holes of the fixation stent. The drainage tubes may also simply be larger in diameter on one side compared to the other side to produce a wedge fit upon insertion.

The fixation stent and drainage tubes may be produced from the following examples of biocompatible materials: nitinol, stainless steel, tantalum, gold, titanium, platinum, polyimide, silicone, Teflon, polypropylene, perfluoroalkoxy, fluorinated ethylene-propylene, carbothane, polyurethanes, polyethylenes, acrylic, collamer, or nylon. Other biocompatible materials or a combination of the aforementioned materials are contemplated as well.

The fixation stent and drainage tubes may also be treated with, or coated in, a biocompatible coating to improve biocompatibility, facilitate fluid flow, prevent infection, and/or for any other reason. Suitable treatment or coating materials include but are not limited to albumin, rapamycin, polyethylene glycol, tacrolimus, anti-fibrotic drugs, anti-fouling agents, or fibronectin. Other biocompatible agents or a combination of the aforementioned agents are possible as well.

The fixation stent may be of any suitable length. For example, the fixation stent may have a length of less than or equal to 30 mm, less than or equal to 20 mm, less than or equal to 18 mm, less than or equal to 16 mm, less than or equal to 14 mm, less than or equal to 12 mm, less than or equal to 10 mm, less than or equal to 8 mm, less than or equal to 6 mm, less than or equal to 5 mm. In some embodiments, the fixation stent has a length of greater than or equal to 5 mm, greater than or equal to 8 mm, greater than or equal to 10 mm, greater than or equal to 12 mm, greater than or equal to 14 mm, or greater than or equal to 16 mm. Combinations of the above-referenced ranges are also possible (e.g., greater than or equal to 5 mm and less than or equal to 20 mm). Other ranges are also possible.

In some embodiments, the fixation stent may have an outer diameter of less than or equal to 1 mm, less than or equal to 800 µm, less than or equal to 750 µm, less than or equal to 700 µm, less than or equal to 650 µm, less than or equal to 600 µm, less than or equal to 550 µm, less than or equal to 500 µm, less than or equal to 450 µm, less than or equal to 400 µm, less than or equal to 350 µm, less than or equal to 300 µm, less than or equal to 250 µm, less than or equal to 200 µm, less than or equal to 150 µm, or less than or equal to 100 µm. In some embodiments, the fixation stent has an outer diameter of greater than or equal to 100 µm, greater than or equal to 200 µm, greater than or equal to 300 µm, greater than or equal to 400 µm, greater than or equal to 500 µm, greater than or equal to 600 µm, or greater than or equal to 700 µm. Combinations of the above-referenced ranges are also possible (e.g., greater than or equal to 100 µm and less than or equal to 800 µm). Other ranges are also possible.

In some embodiments in which the fixation stent is a hollow tube, the fixation stent may have an inner diameter of less than or equal to 1 mm, less than or equal to 800 µm, less than or equal to 750 µm, less than or equal to 700 µm, less than or equal to 650 µm, less than or equal to 600 µm, less than or equal to 550 µm, less than or equal to 500 µm, less than or equal to 450 µm, less than or equal to 400 µm, less than or equal to 350 µm, less than or equal to 300 µm, less than or equal to 250 µm, less than or equal to 200 µm, less than or equal to 150 µm, or less than or equal to 100 µm. In some embodiments, the fixation stent has an inner diameter of greater than or equal to 100 µm, greater than or equal to 200 µm, greater than or equal to 300 µm, greater than or equal to 400 µm, greater than or equal to 500 µm, greater than or equal to 600 µm, or greater than or equal to 700 µm. Combinations of the above-referenced ranges are also possible (e.g., greater than or equal to 200 µm and less than or equal to 700 µm). Other ranges are also possible.

In some embodiments in which the fixation stent is a hollow tube, the fixation stent may have an outer diameter of 400 µm and an inner diameter of 300 µm, although it should be appreciated that any combination of outer and inner diameters described above may be possible as long as the outer diameter is larger than the inner diameter.

The drainage tubes could be 5 mm in length, but could be less than or equal to 10 mm, less than or equal to 8 mm, less than or equal to 6 mm, less than or equal to 4 mm, less than or equal to 2 mm, or less than or equal to 1 mm. Combinations of the above-referenced ranges are also possible (e.g., greater than or equal to 1 mm and less than or equal to 10 mm). Other ranges are also possible.

In embodiments where the drainage tubes are hollow tubes, the drainage tube may have an outer diameter of 350 µm. However, outer diameters of less than or equal to 800 µm, less than or equal to 750 µm, less than or equal to 700 µm, less than or equal to 650 µm, less than or equal to 600 µm, less than or equal to 550 µm, less than or equal to 500 µm, less than or equal to 450 µm, less than or equal to 400 µm, less than or equal to 350 µm, less than or equal to 300 µm, less than or equal to 250 µm, less than or equal to 200 µm, less than or equal to 150 µm, or less than or equal to 100

μm are also possible as long as the outer diameter is larger than the inner diameter and the drainage tube is smaller in outer diameter than the corresponding fixation stent. In some embodiments, the drainage tube has an outer diameter of greater than or equal to 100 μm, greater than or equal to 200 μm, greater than or equal to 300 μm, greater than or equal to 400 μm, greater than or equal to 500 μm, greater than or equal to 600 μm, or greater than or equal to 700 μm. Combinations of the above-referenced ranges are also possible (e.g., greater than or equal to 200 μm and less than or equal to 700 μm).

In embodiments where the drainage tubes are hollow tubes, the drainage tube may have an inner diameter of 250 μm. However, inner diameters of less than or equal to 800 μm, less than or equal to 750 μm, less than or equal to 700 μm, less than or equal to 650 μm, less than or equal to 600 μm, less than or equal to 550 μm, less than or equal to 500 μm, less than or equal to 450 μm, less than or equal to 400 μm, less than or equal to 350 μm, less than or equal to 300 μm, less than or equal to 250 μm, less than or equal to 200 μm, less than or equal to 150 μm, less than or equal to 100 μm, or less than or equal to 50 μm are also possible as long as the outer diameter of the drainage tube is larger than the inner diameter drainage tube. Other ranges are also possible. In some embodiments, the drainage tube has an outer diameter of greater than or equal to 50 μm, greater than or equal to 100 μm, greater than or equal to 200 μm, greater than or equal to 300 μm, greater than or equal to 400 μm, greater than or equal to 500 μm, greater than or equal to 600 μm, or greater than or equal to 700 μm. Combinations of the above-referenced ranges are also possible (e.g., greater than or equal to 50 μm and less than or equal to 700 μm).

Embodiments of the modular glaucoma implant manufactured through one or more of the following processes are possible: micro machining, laser machining, electroforming, sintering, electrical discharge mining, injection molding, compression molding, thermos-forming, 3D printing, solvent casing, or lithography. However, other methods of production are possible as well.

Flow Simulations

Figure 9A:
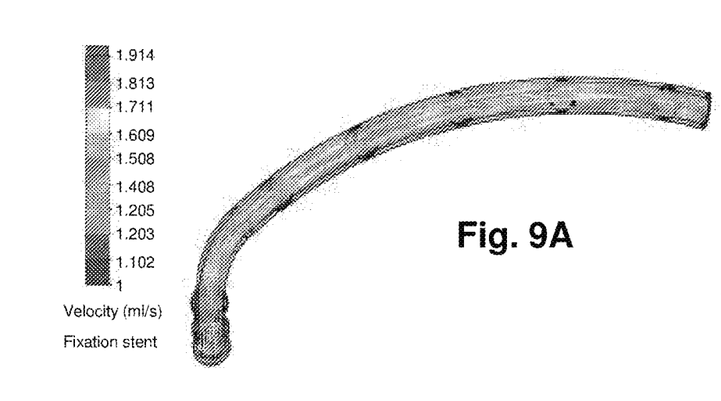
FIG. 9A is a flow trajectory model visualizing simulated aqueous humor flow through the fixation stent of the modular glaucoma implant according to one embodiment.
Figure 9B:
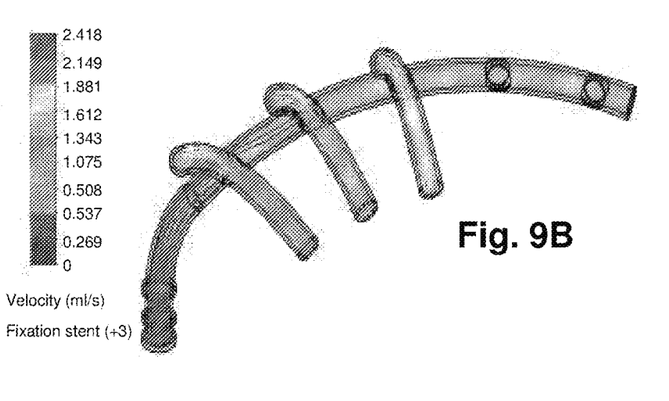
FIG. 9B is a flow trajectory model visualizing simulated aqueous humor flow through the drainage tubes of the modular glaucoma implant according to the embodiment of FIG. 9A.
Figure 9C:
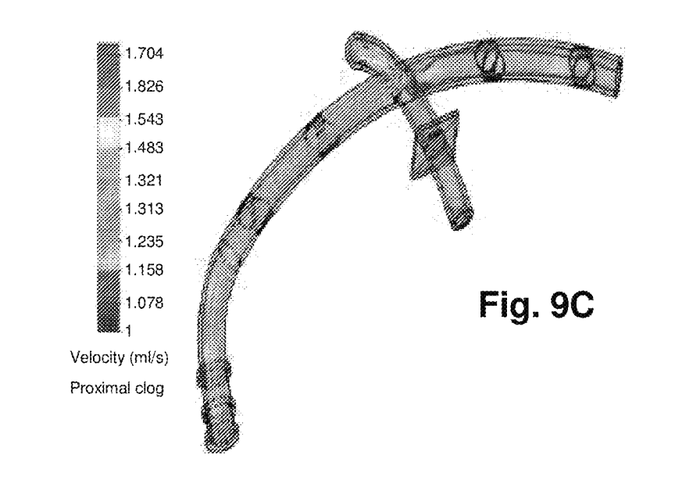
FIG. 9C is a flow trajectory model visualizing simulated aqueous humor flow through the modular glaucoma implant according to the embodiment of FIG. 9A when the device experiences a blockage in a first end of a drainage tube.
Figure 9D:
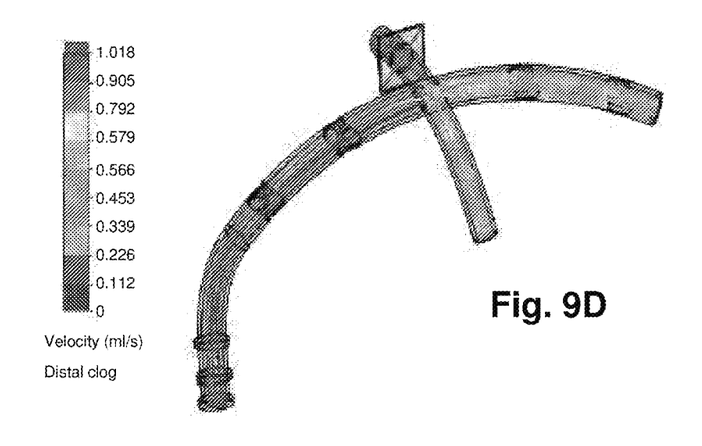
FIG. 9D is a flow trajectory model visualizing simulated aqueous humor flow through the modular glaucoma implant according to the embodiment of FIG. 9A when the device experiences a blockage in a second end of a drainage tube.
Figure 10:
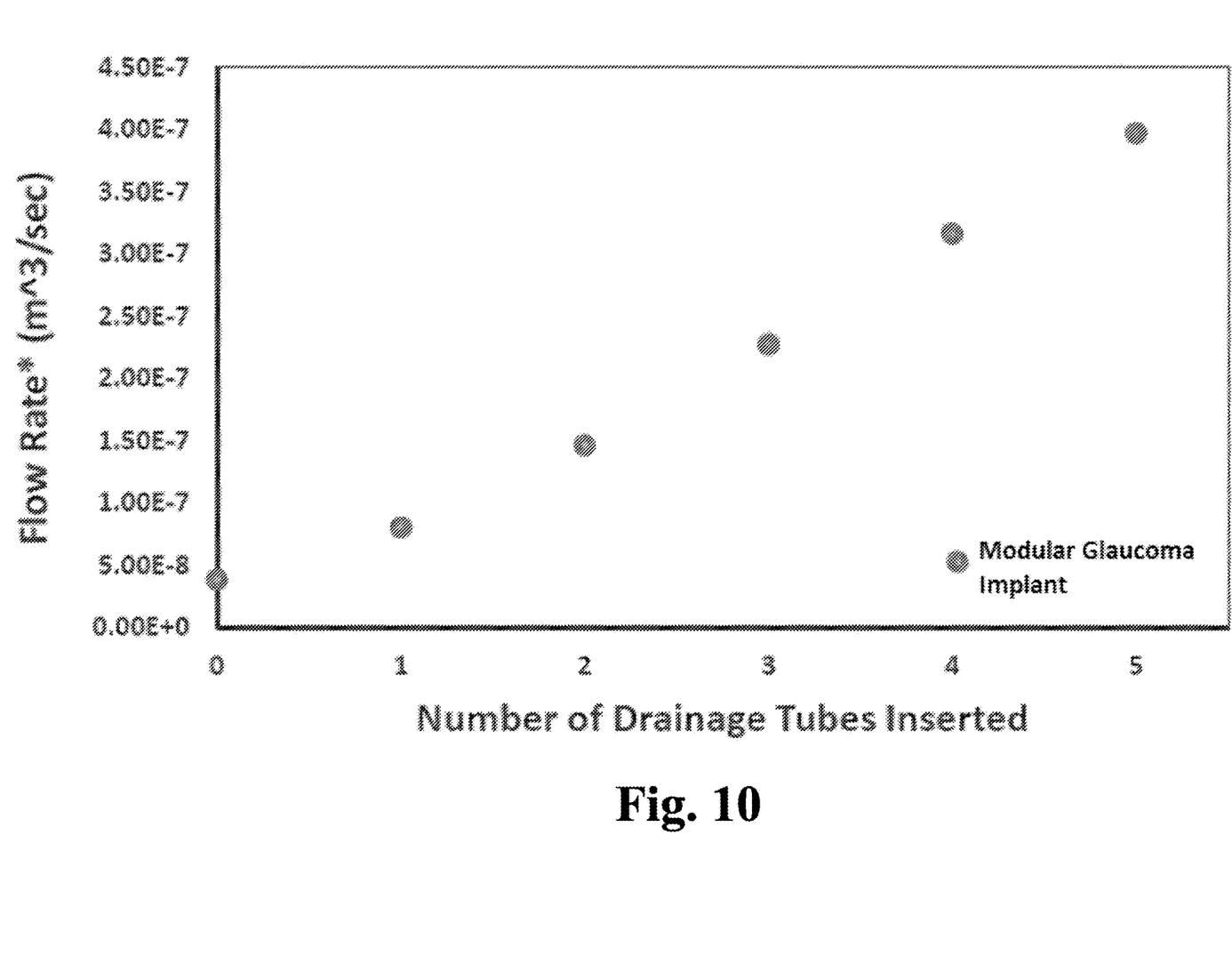
FIG. 10 is a plot showing the flow rate of simulated aqueous humor through one embodiment of the modular glaucoma implant versus the number of drainage tubes inserted.

FIGS. 9 and 10 show flow simulations involving the devices described herein. To test the viability of the modular glaucoma implant, SolidWorks Flow Simulation was used to model flow of aqueous humor from the anterior chamber to the suprachoroidal space and/or the Schlemm's Canal. Values of volumetric flow rate out of the anterior chamber were obtained from the simulations and graphed in FIG. 10. In order to accurately represent the flow through the device, average values for pressures in the anterior chamber, suprachoroidal space, and the Schlemm's Canal; 3333.06 Pa, 106.66 Pa, and 1402.35 Pa respectively were used. Maepea, O. and Bill, A., 1989, "The pressures in the episcleral veins, Schlemm's canal and the trabecular meshwork in monkeys: effects of changes in intraocular pressure", Experimental Eye Research, 49(4). Emi, K. et al., 1989, "Hydrostatic pressure of the suprachoroidal space", Investigative Ophthalmology& Visual Science, 30(2).

Individual flow trajectory models as seen in FIGS. 9A to 9D, were used to qualitatively visualize the performance of design. FIG. 9A shows the flow profile of aqueous humor when the device is unobstructed. FIG. 9B shows aqueous humor flow through the device with three drainage tubes inserted with flow entering only the suprachoroidal space. FIG. 9C shows flow of aqueous humor through the device when a single drainage tube becomes clogged at the inflow end of the drainage tubes. Finally, FIG. 9D shows aqueous humor flow through the device with a clog in the outflow end of a single drainage tube.

This qualitative analysis lead to the following findings:

Analyzing the flow trajectories confirmed that the modular glaucoma implant design would be more resistant to reduced flow in the case of stent/tube clogging. This is a result of providing access to both the Schlemm's Canal and the suprachoroidal space.

As shown in FIG. 9C, if there is a clog of the drainage tube in the inflow end, flow can instead pass through the fixation stent inflow aperture and easily enter the suprachoroidal space through the outflow end of the drainage tube. Alternatively, as shown in FIG. 9D, if there is a clog of the drainage tube in the outflow end, aqueous humor can pass through both the fixation stent and the inflow end of the drainage tube, emptying into the Schlemm's Canal. This effect is only enhanced when multiple drainage tubes are inserted.

Finally, as mentioned above, insertion of more drainage tubes yields more flow out of the anterior chamber as charted in FIG. 10. Accordingly, this would easily allow the surgeons to customize the amount of flow desired for the particular patient.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the embodiments described herein may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Further, some actions are described as taken by a "user" or a "surgeon." It should be appreciated that a "user" or a "surgeon" need not be a single individual, and that in some embodiments, actions attributable to a "user" or "surgeon" may be performed by a team of individuals and/or an individual in combination with computer-assisted tools or other mechanisms.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention. All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A device for implanting into an eye, comprising:
a curved fixation stent having a first end and a second end separated by the length of the fixation stent, the curved fixation stent including one or more through-holes across a width of the curved fixation stent from a first side to a second side of the curved fixation stent, wherein at least a portion of the curved fixation stent has a cylindrical cross-section; and
a first drainage tube with a first end and a second end, constructed and arranged to be insertable into one of the one or more through-holes in the curved fixation stent,
wherein a first fluid flow path for fluid to enter or exit the device exists between the first and second ends of the curved fixation stent, and inserting the first drainage tube into the curved fixation stent creates a second fluid flow path transverse to the first fluid flow path,
wherein the first drainage tube comprises a bulge in between the first end and the second end of the first drainage tube, and
wherein the bulge snap-fits with a through-hole of the one or more through-holes of the curved fixation stent.

2. A device for implanting into an eye, comprising:
a curved fixation stent having a first end and a second end across a length of the curved fixation stent, and a first side and a second side across a width of the curved fixation stent, wherein at least a portion of the curved fixation stent has a cylindrical cross-section; and
a first drainage tube having a first end and second end, constructed and arranged such that a first end of the first drainage tube extends from the first side of the curved fixation stent, and the second end of the first drainage tube extends from the second side of the curved fixation stent,
wherein the first drainage tube comprises a bulge in between the first end and the second end of the first drainage tube, and
wherein the bulge snap-fits with a through-hole of the curved fixation stent.

3. The device of claim 1, wherein when the first drainage tube is inserted into the curved fixation stent, the first end of the drainage tube extends from the first side of the curved fixation stent, and the second end of the drainage tube extends from the second side of the curved fixation stent.

4. The device of claim 2, wherein the curved fixation stent comprises one or more through-holes along the width of the curved fixation stent.

5. The device of claim 2, wherein the device is constructed and arranged to facilitate fluid flow through a first fluid flow path through the curved fixation stent from the first end of the curved fixation stent to the second end of the curved fixation stent.

6. The device as in claim 1, further comprising a second drainage tube, constructed and arranged such that a first end of the second drainage tube extends from the first side of the curved fixation stent, and a second end of the second drainage tube extends from the second side of the curved fixation stent.

7. The device as in claim 6, further comprising a third drainage tube, constructed and arranged such that a first end of the third drainage tube extends from the first side of the curved fixation stent, and a second end of the third drainage tube extends from the second side of the curved fixation stent.

8. The device as in claim 1, wherein the curved fixation stent is constructed and arranged include a second fluid flow path, transverse to the first fluid flow path, through the first drainage tube.

9. The device as in claim 1, wherein the first drainage tube is curved about a different axis than the curved fixation stent.

10. The device as in claim 1, wherein the first drainage tube is removable from the curved fixation stent.

11. The device as in claim 1, wherein the first drainage tube comprises through-holes in the bulge, allowing flow from the first end of the curved fixation stent to the second end of the curved fixation stent.

12. The device as in claim 1, wherein the first drainage tube comprises a plurality of fenestrations at the second end of the first drainage tube.

13. The device as in claim 1, further comprising retention rings extending substantially circumferentially from the first end of the curved fixation stent.

14. The device as in claim 1, wherein the curved fixation stent is made of a biocompatible material comprising one or more of: polyimide, silicone, Teflon, polypropylene, perfluoroalkoxy, fluorinated ethylene-propylene, carbothane, polyurethanes, polyethylenes, acrylic, collamer, nylon, nitinol, stainless steel, tantalum, gold, titanium, or platinum.

15. The device as in claim 1, wherein the device comprises a coating layer comprising one or more of: albumin, rapamycin, polyethylene glycol, tacrolimus, an anti-fibrotic drug, an anti-fouling agent, or fibronectin.

16. The device as in claim 1, wherein the first drainage tube comprises a transverse through-hole between the first end of the first drainage tube and second end of the first drainage tube, allowing a second fluid flow path through the first drainage tube and the first fluid flow path through the curved fixation stent to merge.

17. The device as in claim 1, wherein the curved fixation stent is constructed and arranged to include a third fluid flow path, transverse to the first fluid flow path, through a second drainage tube.

* * * * *